US00PP33877P2

(12) United States Plant Patent
Rouwette

(10) Patent No.: US PP33,877 P2
(45) Date of Patent: Jan. 18, 2022

(54) ***HYDRANGEA* PLANT NAMED 'GRHPLS'**

(50) Latin Name: *Hydrangea paniculala*
Varietal Denomination: GRHPLS

(71) Applicant: Guido Rouwette, Valkenburg (NL)

(72) Inventor: Guido Rouwette, Valkenburg (NL)

( * ) Notice: Subject to any disclaimer, the term of this patent is extended or adjusted under 35 U.S.C. 154(b) by 0 days.

(21) Appl. No.: 17/100,284

(22) Filed: Nov. 20, 2020

(51) Int. Cl.
*A01H 5/02* (2018.01)
*A01H 6/48* (2018.01)

(52) U.S. Cl.
USPC ..... Plt./250

(58) Field of Classification Search
USPC ..... Plt./250
CPC ..... A01H 5/02; A01H 5/00; A01H 6/48
See application file for complete search history.

(56) References Cited

PUBLICATIONS

Andre-Briant *Hydrangea paniculata* Little Spooky GRHP08, retrieved on Mar. 23, 2021, retrieved from the Internet at https://www.andre-briant.fr/en/variety-range/access-to-varieties/novelties/4631-hydrangea-paniculata-little-spooky-grhp08-.html, 2 pp. (Year: 2021).*

* cited by examiner

*Primary Examiner* — June Hwu
(74) *Attorney, Agent, or Firm* — Penny J. Aguirre

(57) ABSTRACT

A new cultivar of *Hydrangea paniculata* plant named 'GRHPLS' that is characterized by its inflorescences with flowers that are creamy white in color and remain creamy white as they mature (they do not turn pink), its very compact and densely branched plant habit, and its dense panicles with sturdy sterile flowers.

2 Drawing Sheets

Botanical classification: *Hydrangea paniculata.*
Varietal denomination: 'GRHPLS'.

BACKGROUND OF THE INVENTION

The present invention relates to a new and distinct cultivar of *Hydrangea paniculata* and will be referred to hereafter by its cultivar name, 'GRHPLS'. 'GRHPLS' represents a new panicle *Hydrangea*, a perennial shrub grown for landscape use.

The new *Hydrangea* resulted from a controlled breeding program conducted by the Inventor in Valkenburg, The Netherlands. The objectives of the breeding program were to develop new cultivars of *Hydrangea paniculata* with sturdy stems, healthy foliage, and unique flower colors. The Inventor made crosses in 2011 between unnamed and unpatented proprietary plants of *Hydrangea paniculata* in the Inventor's breeding program as both the female parent and male parent. The exact characteristics of the parents are unknown as seeds were pooled and sown from several crosses. 'GRHPLS' was selected as a single unique plant in summer of 2014 from the resulting seedlings of the above crosses.

Asexual propagation of the new cultivar was first accomplished by stem cuttings by the Inventor in summer of 2014 in Valkenburg, The Netherlands. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'GRHPLS' as a unique cultivar of *Hydrangea.*

1. 'GRHPLS' exhibits inflorescences with flowers that are creamy white in color and remain creamy white as they mature (they do not turn pink).
2. 'GRHPLS' exhibits a very compact and densely branched plant habit.
3. 'GRHPLS' exhibits dense panicles with sturdy sterile flowers.

'GRHPLS' can be most closely compared to the *Hydrangea paniculata* cultivars 'Limelight' (U.S. Plant Pat. No. 12,874), 'GRHP08' (not patented) and 'Silver Dollar' (not patented). 'Limelight' is similar to 'GRHPLS' in having dense flower panicles and a well-branched plant habit (floriferous). 'GRHP08' is similar to 'GRHPLS' in inflorescence color and in having a compact plant habit. 'GRHP08' differs from 'GRHPLS' in having longer stems and becoming taller in height when grown in the landscape, slighter larger and more pointed inflorescences, and a slightly more open plant habit. 'Silver Dollar' is similar to 'GRHPLS' in being floriferous and in having a well-branched plant habit. 'Limelight' and 'Silver Dollar' both differ from 'GRHPLS' in having less compact plant habits and flowers that change to a light pink color as they mature.

BRIEF DESCRIPTION OF THE DRAWINGS

The accompanying colored photographs illustrate the overall appearance and distinct characteristics of the new *Hydrangea*. The photographs were taken of a two-year-old plant of 'GRHPLS' as grown outdoors in a 27-cm container in Boskoop, The Netherlands.

The photograph in FIG. 1 provides a side view of the plant habit of 'GRHPLS' in bloom.

Figure 1:
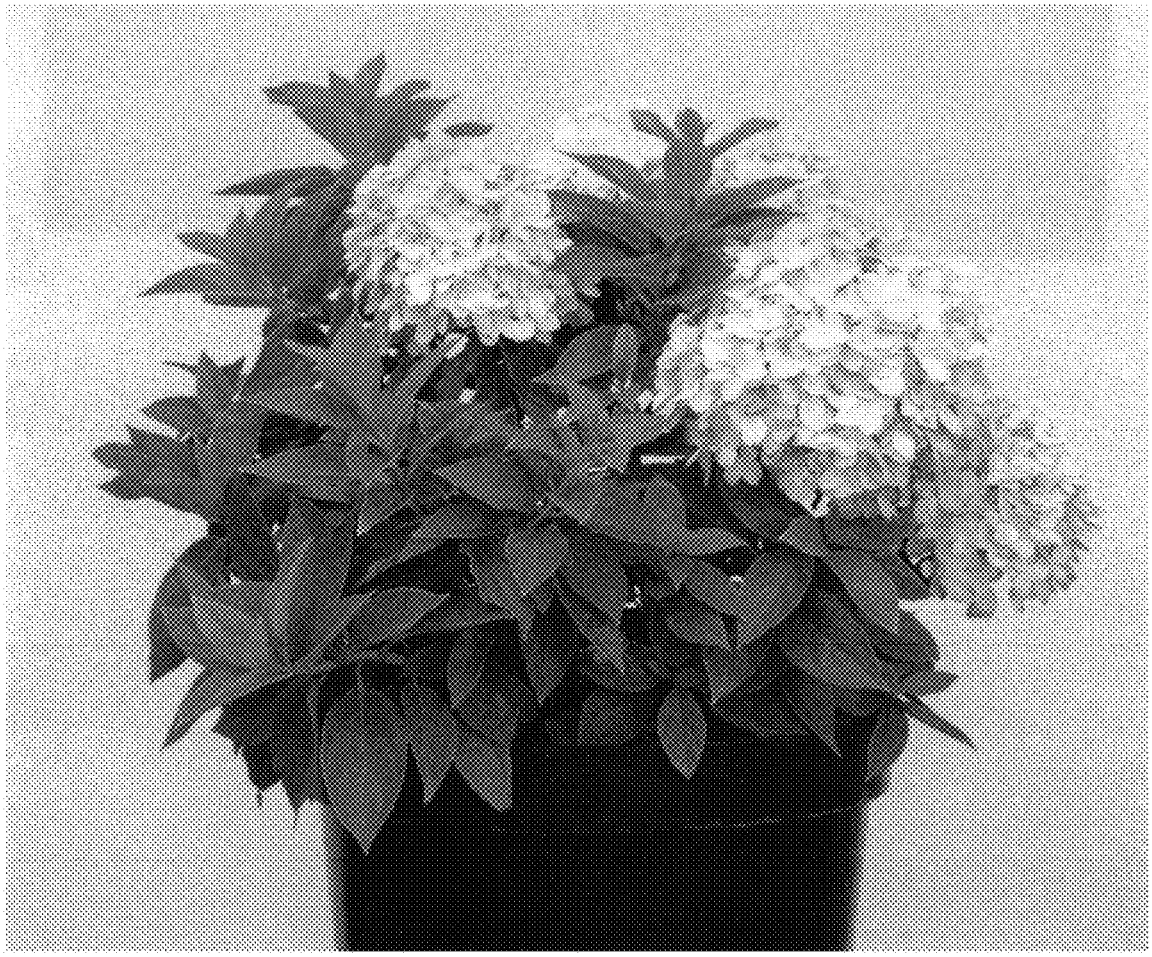
Figure 2:
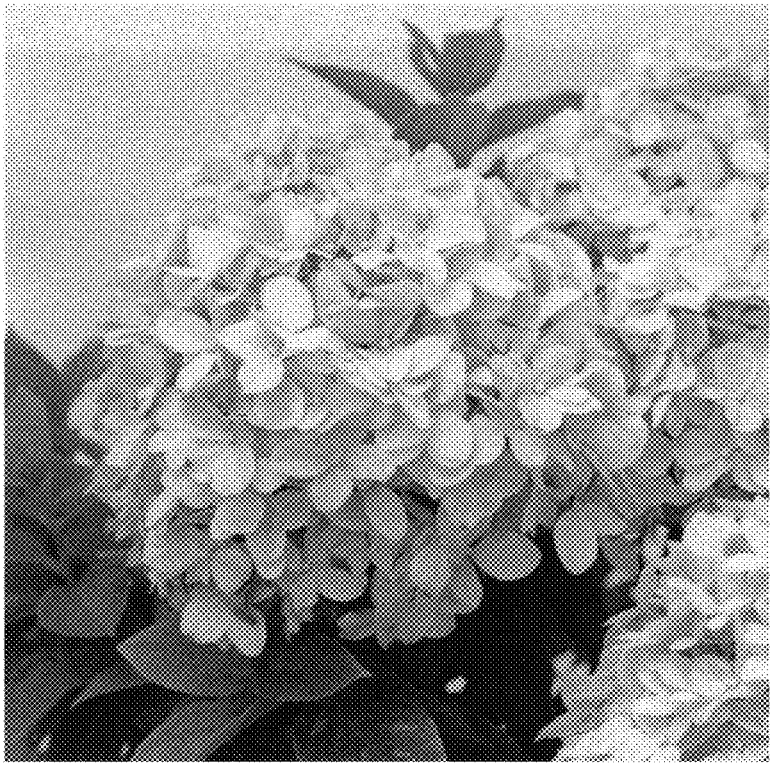

The photograph in FIG. 2 provides a close-up view of an inflorescence of 'GRHPLS'.

Figure 3:
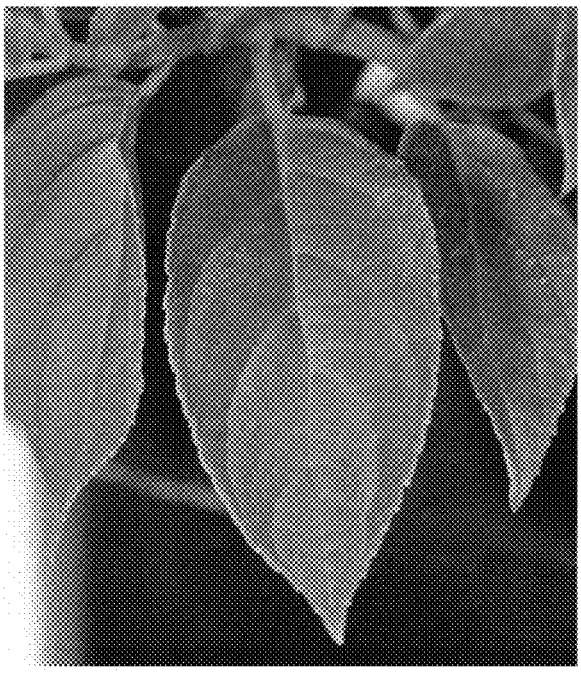

The photograph in FIG. 3 provides a close-up view of the foliage of 'GRHPLS'.

The colors in the photographs are as close as possible with the photographic and printing technology utilized and the color values cited in the detailed botanical description accurately describe the colors of the new *Hydrangea.*

BOTANICAL DESCRIPTION OF THE PLANT

The following is a detailed description of two-year-old plants of 'GRHPLS' as grown outdoors in 27-cm containers in Boskoop, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period.*—July through September in The Netherlands.

*Plant type.*—Deciduous shrub, panicle type *Hydrangea.*

*Plant habit.*—Broadly upright and very compact.

*Height and spread.*—Reaches 32.5 cm in height and 46 cm in spread as a two-year-old plant in a container and up to 60 cm in height and 46 cm in spread as a two-year-old plant in the landscape.

*Hardiness.*—At least in U.S.D.A. Zones 4 to 9.

*Diseases and pests.*—No susceptibility and resistance to diseases or pests has been observed.

*Root description.*—Fine, fibrous and dense, NN155A and 164A in color.

*Propagation.*—Stem cuttings.

*Root development.*—6 to 8 weeks for root initiation with a finished plant produced in in a P9 container in about 12 months from a rooted cutting.

*Growth rate and vigor.*—Low to moderate.

Stem description:

*Stem shape.*—Rounded.

*Stem strength.*—Strong.

*Stem color.*—Young; 145A to 145B, mature; 199B to 199D, old bark; 197B and 199B.

*Stem size.*—Average of 46.6 cm in length (excluding inflorescence) and 4 mm in diameter.

*Stem surface.*—Young stems are matte and densely covered with short stiff hairs; an average of 0.5 mm in length that match surface color, mature stems are matte and moderately covered with lenticels; an average of 1.5 mm in length and 0.75 mm in width, 199D in color, mature bark is mostly smooth and lacks fasciation.

*Stem aspect.*—Upright, average of 55° to soil level, varying between 20° and 90°.

*Internode length.*—An average of 1.5 cm.

*Branching.*—Freely branching with an average of 30 lateral branches.

Foliage description:

*Leaf shape.*—Ovate to narrow ovate.

*Leaf arrangement.*—Opposite or in whorls of three.

*Leaf division.*—Simple.

*Leaf base.*—Obtuse to short attenuate.

*Leaf apex.*—Apiculate.

*Leaf margins.*—Serrate.

*Leaf venation.*—Pinnate, color; upper surface 144A, lower surface 145B.

*Leaf size.*—An average of 7 cm in length and 3.8 cm in width.

*Leaf attachment.*—Petiolate.

*Leaf number.*—An average of 16 per lateral stem.

*Leaf surface.*—Both surfaces; smooth and very slightly rugose, both surfaces sparsely to moderately covered with short adpressed strigose hairs; average of 0.3 mm in length, 157D in color.

*Leaf color.*—Young upper surface; 144A to 144B, young lower surface 144B, mature upper surface; between 137A and NN137B, mature lower surface; 147B, fall color is non-showy and about 137C in color on the upper surface and 147D on the lower surface.

*Petioles.*—An average of 1 cm in length and 2.5 mm in diameter, upper surface color 144C, proximal end 144B, lower surface color 144C, proximal end 144A, both surfaces matte and sparsely covered with very short hairs an average of 0.3 mm in length and too small to measure color.

Inflorescence description:

*Inflorescence type.*—Terminal conical panicle, comprised of sterile flowers above inconspicuous fertile flowers, broadly conical to nearly globose in shape.

*Lastingness of inflorescence.*—Sterile flowers; persistent for an average of 6 weeks, fertile flowers; self-cleaning, an average of 5 days.

*Inflorescence number.*—One per lateral stem.

*Inflorescence size.*—An average of 12.9 cm in height and 13.8 cm in diameter.

*Flower number.*—An average of 400 sterile flowers and 200 fertile flowers per panicle.

*Flower fragrance.*—None.

*Flower aspect.*—Sterile flowers; held upright to outward and slightly drooping, fertile flowers; held upright from peduncle.

*Flower size.*—Sterile flowers; up to 2.9 cm in diameter and 0.7 mm in depth, fertile flowers; an average of 1.3 cm in diameter and 7 mm in depth.

*Flower type.*—Sterile flowers rotate, fertile flowers rotate and dropped when mature.

*Flower buds.*—Sterile flowers; an average of 0.5 mm in length and 1.3 cm in diameter, broadly cup-shaped, between 145C and 150D in color, fertile flowers; an average of 3 mm in length, 2 mm in diameter, obovate in shape, color; 145D, immature calyx 193A.

*Petals.*—Sterile flowers; 4, not opening, remaining in bud-stage; length of petal 2 mm, glabrous, matte surfaces, upper and lower surface color 157D, fertile flowers; 5, rotate and cruciform in shape, ovate to concave in shape, acute apex, cuneate base, entire margins, average of 4 mm in length and 2.5 mm in width, upper surface glabrous and slightly glossy, lower surface glabrous and matte, color; when opening and fully open upper and lower surface NN155D, petals drop at maturity.

*Peduncles.*—Primary peduncles; strong, flattened oval in shape, an average of 3 cm in length and 2 mm in width. secondary peduncles 2 cm in length and 2 mm in width, 157A in color, surface is matte and moderately covered with thin pubescence; hairs an average of 0.3 mm in length and 145D in color.

*Pedicels.*—Sterile flowers; moderate strength, an average of 2.5 cm in length and 1 mm in width, color; 157D, proximal end 157A, held at a 45° angle, surface is matte and moderately covered with thin pubescence an average of 0.3 mm in length and 157D in color, fertile flowers; moderate strength, an average of 2 mm in length, 0.5 mm in diameter, held at a 30° angle, 145D in color, surface is matte and densely covered with thin pubescence; hairs an average of 0.3 mm in length and 145D in color.

*Sepals.*—Sterile flowers; 4 (occasionally 3 or 5), rotate, ovate to obovate, slightly carinate in shape, very weakly overlapping, obtuse apex, cuneate base, entire margins, average of 1.7 cm in length and 1.5 cm in width, both surfaces; glabrous and matte, color; upper surface when opening slightly darker than 150D, yet lighter than 150C, lower surface when opening 150D, upper and lower surface when fully open 150D and 155A, fading to 145B, fertile flowers; 5, rotate, broadly deltoid in shape, broad acuminate apex, broad cuneate base, entire margins, 1 mm in length, 1.5 mm in width, both surfaces glabrous and matte, color; when opening upper surface 193B, when opening lower surface 193A to 193B, when fully open upper surface and lower surface 145C.

*Bracts.*—1 present on each pedicel, narrow elliptic in shape, acute apex, acute base, entire margins, 7 mm in length, 2 mm in width, both surfaces 145B in color, both surfaces glabrous.

Reproductive organs:

*Gynoecium.*—Sterile flowers; none observed, fertile flowers; 3 pistils, an average of 2 mm in length, stigma; club-shaped and 157D in color, style; 1 mm in length, 145D in color, ovary is 147D in color.

*Androecium.*—Sterile flowers; none observed, fertile flowers; stamens; average of 10, filaments; 6 mm in length, NN155D in color, anthers; broad oblong in shape, 0.5 mm in length, 150D in color, pollen; moderate quantity, 156C in color.

*Fruit and seed.*—None observed to date.

It is claimed:

1. A new and distinct cultivar of *Hydrangea* plant named 'GRHPLS' substantially as herein illustrated and described.

* * * * *